United States Patent [19]

Kruse

[11] Patent Number: 4,798,843
[45] Date of Patent: Jan. 17, 1989

[54] 2-MERCAPROIMIDAZOLE DOPAMINE-β-HYDROXYLASE INHIBITORS

[75] Inventor: Lawrence I. Kruse, Tewin, England

[73] Assignee: SmithKline Beckman Corporation, Philadelphia, Pa.

[21] Appl. No.: 71,515

[22] Filed: Jul. 9, 1987

[51] Int. Cl.$^4$ .................. A61K 31/415; C07D 233/84
[52] U.S. Cl. .................................. 514/392; 514/398; 548/317; 548/322; 548/337
[58] Field of Search ...................... 548/317, 322, 337; 514/392, 398

[56] References Cited

U.S. PATENT DOCUMENTS 4,104,383 8/1978 Krausz ........................... 564/342 X

OTHER PUBLICATIONS

Maeda, S. et al., *Chem. Pharm. Bull.* 1984, 32(7), 2536–43.
*Chemical Abstracts*, 101:211047m (1984)[Maeda, S., et al., *Chem. Pharm. Bull.* 1984, 32(7), 2536–43].
*Chemical Abstracts*, 100:209694g (1984)[Isomura, Y., et al., *Chem. Pharm. Bull.* 1984, 32(1), 152–65].
*Chemical Abstracts*, 89:146836m (1978)[Yamazaki, C., et al., *Bull. Chem. Soc. Jpn.* 1978, 51(6), 1846–55].
*Chemical Abstracts*, 77:14750w (1972)[Jensen, N., et al., *J. Med. Chem.* 1972, 15(4), 341–4].
*Chemical Abstracts*, 72:31698z (1970)[Arens, A., et al., *Khim. Geterotsikl. Soedin.* 1969, (4), 719–22].
*Chemical Abstracts*, 69:38155s (1968)[Balezin, S., et al., *Bor'Ba. Korroz. Khim. Neftepererab. Prom.*, 1967, No. 1, 98–103].

*Primary Examiner*—Richard A. Schwartz
*Attorney, Agent, or Firm*—Stuart R. Suter; Alan D. Lourie; Janice E. Williams

[57] ABSTRACT

Potent dopamine-β-hydroxylase inhibitors having the Formula

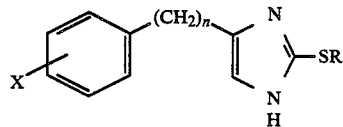

that are useful to inhibit dopamine-β-hydroxylase activity, pharmaceutial compositions including these inhibitors, and methods of using these inhibitors to inhibit dopamine-β-hydroxylase activity in mammals. Also disclosed are novel intermediates useful in preparing the presently invented inhibitors.

18 Claims, No Drawings

2-MERCAPROIMIDAZOLE DOPAMINE-β-HYDROXYLASE INHIBITORS

FIELD OF THE INVENTION

This invention relates to novel compounds that inhibit dopamine-β-hydroxylase.

BACKGROUND OF THE INVENTION

In the catecholamine biosynthetic pathway, tyrosine is converted in three steps to norepinephrine (NE). Intermediates are dihydroxyphenylalanine (DOPA) and dopamine (DA). Dopamine is hydroxylated to norepinephrine by dopamine-β-hydroxylase (DBH) in the presence of oxygen and ascorbic acid.

Inhibition of catecholamine activity decreases blood pressure. Weinshilboum, *Mayo Clin. Proc.* 55, 39 (1980), reviews compounds that inhibit catecholamine activity by acting upon adrenergic receptors. Alternatively, the catecholamine biosynthetic pathway can be suppressed at any of the three steps, resulting in reduced NE levels. In addition to producing an antihypertensive effect, inhibitors of NE synthesis are active as diuretics, natriuretics, cardiotonics, and vasodilators. Inhibition of DBH activity can have the added advantage of increasing DA levels, which as reported by Ehrreich et al., "New Antihypertensive Drugs," Spectrum Publishing, 1976, pp. 409–432, has selective vasodilator activity at certain concentrations.

DBH inhibitors also have been shown to reduce or prevent formation of gastric ulcers in rats by Hidaka et al., "Catecholamine and Stress," edit. by Usdin et al., Permagon Press, Oxford, 1976, pp. 159–165 and by Osumi et al., *Japan J. Pharmacol.* 23, 904 (1973).

A number of DBH inhibitors are known. These generally are divided into two classes, namely, metal chelating agents, which bind copper in the enzyme, and phenethylamine analogues. Rosenberg et al., "Essays in Neurochemistry and Neuropharmacology," Vol. 4, ed. by Youdim et al., John Wiley & Sons, 1980, pp. 179–192, and Goldstein, *Pharmacol. Rev.* 18(1), 77 (1966), review DBH inhibitors. The former report that many potent DBH inhibitors have a hydrophobic side chain of size comparable to the aromatic ring of DA, leading the authors to suggest that incorporation of a terminal hydroxyl group on a 4- to 6- carbon side chain on a phenethylamine analogue may yield potent inhibitors.

Known DBH inhibitors include:
(a) 5-alkylpicolinic acids [See, Suda et al., *Chem. Parm. Bull.* 17, 2377 (1969); Umezawa et al., *Biochem. Pharmacol.* 19, 35 (1969); Hidaka et al., *Mol. Pharmacol.* 9, 172 (1973); Miyano et al., *Chem. Pharm. Bull.* 26, 2328 (1978); Miyano et al., *Heterocycles* 14, 755 (1980); Claxton et al., *Eur. J. Pharmacol.* 37, 179 (1976)];
(b) BRL 8242 [See Claxton et al., *Eur J. Pharmacol.* 37, 179 (1976)];
(c) 1-alkylimidazole 2 thiols [See, Hanlon et al., *Life Sci.* 12, 417 (1973); Fuller et al., *Adv. Enzyme Regul.* 15, 267 (1976)];
(d) substituted thioureas [See, Johnson et al., *J. Pharmacol. Exp. Ther.* 168, 229 (1969)]; and
(e) benzyloxyamine and benzylhydrazine [See, Creveling et al., *Biochim. Biophys. Acta* 64, 125 (1962); Creveling et al., *Biochim. Biophys. Acta* 8, 215 (1962); Van Der Schoot et al., *J. Pharmacol. Exp. Ther.* 141, 74 (1963); Bloom, *Ann. N.Y. Acad. Sci.* 107, 878 (1963)].

All the above compounds except benzyloxyamine and benzylhydrazine apparently owe their inhibitory effect to metal chelating properties. Alkyl derivatives of imidazole-2-thiol are more potent, presumably due to non-specific interaction of the alkyl substituent with the enzyme. Benzyloxyamine and benzylhydrazine are phenethylamine analogues which apparently act as competitive inhibitors.

In addition to the above compounds, Runti et al., *Il Farmaco Ed. Sci.* 36, 260 (1980), report that other fusaric acid derivatives and analogues inhibit DBH. These include phenylpicolinic acid, which has twice the inhibitory activity of fusaric acid, and 5 (4 chlorobutyl) picolinic acid, and others such as substituted amides of fusaric acid and acids and amides of 5-butyroylpicolinic acid, 5-aminopicolinic acid and 5-hydrazinopicolinic acid, and derivatives thereof.

Hidaka et al., *Molecular Pharmacology*, 9, 172–177 (1972) report that 5-(3,4-dibromobutyl)picolinic acid and 5-(dimethyldithiocarbamoylmethyl)picolinic acid are DBH inhibitors.

Bupicomide, 5-(n-butyl)picolinamide, is reported by Ehrreich et al., "New Antihypertensive Drugs", Spectrum Publications, 1976, pg. 409–432, to be a DBH inhibitor that has antihypertensive activity.

In European Patent Application No. 125,033 (published Nov. 14, 1984) a series of 1-phenyl and 1-phenylalkylimidazole compounds having a mercapto or alkylthio group in the 2-position are disclosed. These compounds are described as having DBH inhibiting activity.

U.S. Pat. No. 4,487,761 describes several methylpyridine derivatives isolated from the fermentation broth of a strain of Streptoverticillium. These compounds inhibit DBH activity.

U.S. Pat. No. 4,532,331 describes various 1-benzyl-2-aminomethylimidazole derivatives that inhibit DBH activity and includes pharmaceutical compositions containing these derivatives and methods of using these derivatives to inhibit DBH activity.

Non-specific, often toxic effects to known DBH inhibitors have obviated clinical use of these compounds. Fusaric acid, for example, is hepatotoxic. See, for example, Teresawa et al., *Japan. Cir. J.* 35, 339 (1971) and references cited therein. Presumably, the picolinic acid structure interacts with a number of metalloproteins and enzymes non-specifically to produce the observed side effects.

Iverson, *Acta Chem. Scand.* 21, 279 (1967) reports compounds having the formula:

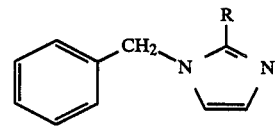

wherein R can be —CO₂H or —CH₂NHC₆H₅, but does not report pharmaceutical uses for the compounds.

In neoprene rubber vulcanization mixtures, 1,3-dihydro 4-phenyl-2H-imidazole-2-thione has been used as a vulcanization accelerator. *CHemical Abstracts* 92:165013u (1980).

SUMMARY OF THE INVENTION

The present invention resides in the discovery that DBH is inhibited by substituted 5-aralkyl-2-mercaptoimidazole and 2-alkylmercaptoimidazole compounds. These compounds are potent and produce prolonged DBH inhibition.

Presently preferred compounds of the invention and compounds included in the pharmaceutical compositions and used in the methods of the invention include: 5-(3,5-difluorobenzyl)-2-mercaptoimidazole, 5-(3,5-dichlorobenzyl)-2-mercaptoimidazole, 5-(4-methoxybenzyl)-2-mercaptoimidazole, and 5-(4-hydroxybenzyl)-2-mercaptoimidazole.

In a further aspect of the invention there are provided novel intermediates useful in preparing substituted 5-aralkyl-2-mercaptoimidazole and 2-alkylmercaptoimidazole compounds.

The invention also is a method of inhibiting DBH activity in mammals, including humans, which comprises administering internally to a subject an effective amount of a substituted 5-aralkyl-2-mercaptoimidazole and 2-alkylmercaptoimidazole compounds.

Included in the present invention are pharmaceutical compositions comprising compounds useful in the method of the invention and a pharmaceutical carrier.

DETAILED DESCRIPTION OF THE INVENTION

The presently invented compounds that inhibit DBH have the following formula:

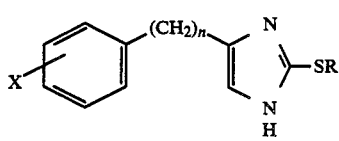

in which:
X is H, F, Cl, Br, I, $C_{1-4}$alkyl, CN, $NO_2$, $SO_2COOH$, OH, CHO, $C_{1-4}$alkoxy, $CH_2OH$, $CH_2OC_{1-4}$alkyl, $CF_3$, $C_2F_5$, $C_3F_7$, $SO_2CH_3$, $SO_2CF_3$, or $CO_2C_aH_{2a+1}$ wherein a is 1–5, or any accessible combination thereof of up to 5 substituents;
n is 0–5; and
R is hydrogen or $C_{1-4}$alkyl; or
any pharmaceutically acceptable salt or hydrate thereof, with the proviso that when X is H, n is not 0.

As used herein, "accessible combination thereof" means any combination of the substituents that is available by chemical synthesis and is stable. $C_{1-4}$alkyl means a straight or branched chain alkyl from 1 to 4 carbons.

It is intended that Formula I compounds in which R is hydrogen include tautomers; that is all compounds wherein the imidazole moiety has one of the below formulae:

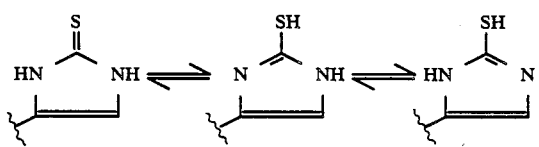

It also is intended that Formula I includes tautomers of the compounds in which R is $C_{1-4}$alkyl, that is compounds wherein the imidazole moiety has either of the below formulae:

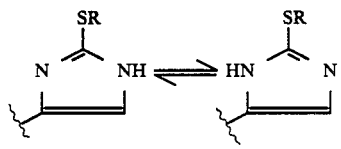

The Formula I compounds areprepared from corresponding phenyl, benzyl, and phenylalkyl acid halides, preferably chlorides by processes such as shown in Scheme I, below. The starting phenyl, benzyl, and phenylalkyl acid halides are known and described in published references or can be obtained readily.

SCHEME I

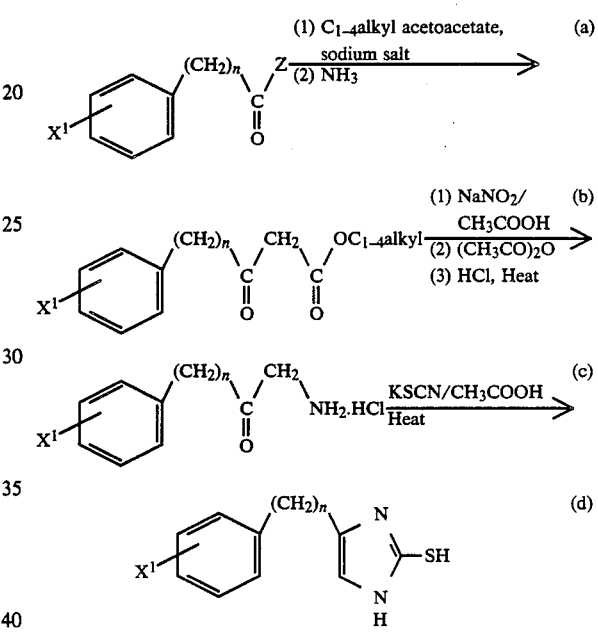

In Scheme I n is as defined in Formula I, $X^1$ is X as in Formula I except OH, and Z is Br, Cl, F, or I. Scheme I depicts addition of a $C_{1-4}$alkyl acetoacetate salt, preferably ethyl acetoacetate sodium salt, to a starting phenylalkyl acid halide, preferably chloride, (a) followed by treatment with a base, preferably ammonia, to yield, after acid work up, compound (b).

Thereafter sodium nitrite in a suitable solvent, preferably water, is added to compound (b) in acetic acid Then, acetic anhydride is added followed by zinc dust to yield a solid. Addition of strong acid, preferably hydrochloric acid, to the solid with heating produces compound (c). Compound (d), a Formula I compound excluding one wherein X is OH, then is prepared by heating a compound (c) with a thiocyanate salt, preferably potassium, in presence of a strong acid, preferably acetic acid.

When desired, Formula I compounds in which X is OH are prepared from a compound (d) wherein $X^1$ is $C_{1-4}$alkoxy using known hydrolysis methods, for example by treatment with boron tribromide, or hydrogen bromide in an appropriate solvent.

Formula I compounds in which R is $C_{1-4}$alkyl, are prepared by alkylating a compound (d) using an appropriate alkyl halide such as methyl iodide or butyl bromide in a $C_{1-4}$alkyl alcohol such as methanol.

In preparing the presently invented compounds of Formula (I), novel intermediate compounds of the following formula were synthesized:

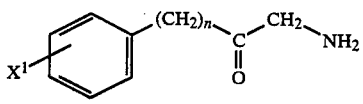

in which:

$X^1$ is H, F, Cl, Br, I, $C_{1-4}$alkyl, CN, $NO_2$, $SO_2NH_2$, COOH, CHO, $C_{1-4}$alkoxy, $CH_2OH$, $CH_2OC_{1-4}$alkyl, $CF_3$, $C_2F_5$, $C_3F_7$, $SO_2CH_3$, $SO_2CF_3$, or $CO_2C_aH_{2a+1}$ wherein a is 1–5, or any accessible combination thereof of up to 5 substituents; and n is 0–5, with the proviso that when $X^1$ is H, n is not 0.

Pharmaceutically acceptable acid addition salts of compounds of Formula I are formed with appropriate organic or inorganic acids by methods known in the art. For example, the base is reacted with a suitable inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Exemplary of the salts which are included in this invention are maleate, fumarate, lactate, oxalate, methanesulfonate, ethanesulfonate, benzenesulfonate, tartrate, citrate, hydrochloride, hydrobromide, sulfate, phosphate, quinate, and nitrate salts.

Compounds of Formula II are included in the invented pharmaceutical compositions and used in the invented methods:

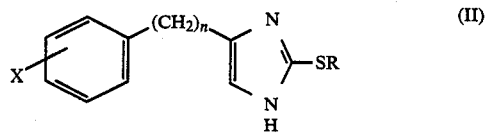

in which:

X is H, F, Cl, Br, I, $C_{1-4}$alkyl, CN, $NO_2$, $SO_2NH_2$, COOH, OH, CHO, $C_{1-4}$alkoxy, $CH_2OH$, $CH_2OC_{1-4}$alkyl, $CF_3$, $C_2F_5$, $C_3F_7$, $SO_2CH_3$, $SO_2CF_3$, or $CO_2C_aH_{2a+1}$ wherein a is 1–5, or any accessible combination thereof of up to 5 substituents;

n is 0–5; and

R is hydrogen or $C_{1-4}$alkyl; or any pharmaceutically acceptable salt or hydrate thereof.

Because the Formula II compounds inhibit DBH activity, they are useful as diuretic, natriuretic, cardiotonic, antihypertensive, and vasodilator agents, as well as antiulcerogenic and anti Parkinsonian agents. Listed in Table I are Formula II compounds that were tested for in vitro DBH inhibition by a standard procedure for assaying conversion of tyramine to octopamine in the presence of DBH. J. J. Pisano, et al., *Biochim. Biophys. Acta*, 43, 566–568 (1960). Octopamine was assayed following sodium periodate oxidation to p-hydroxybenzaldehyde by measuring spectrophotometric absorbance at 330 nm. In Table I, inhibition is given in molar concentration of compound at which DBH activity was halved ($IC_{50}$). Fusaric acid, by this test has an $IC_{50}$ of $8 \times 10^{-7}$ M.

TABLE I

| Compound | DBH $IC_{50}$ |
| --- | --- |
| 5-Phenyl-2-mercaptoimidazole | $5.5 \times 10^{-3}$ |
| 5-(4-Methoxyphenyl)-2-mercaptoimidazole | 38% @ $10^{-4}$ |
| 5-(4-Chlorophenyl)-2-mercaptoimidazole | $1 \times 10^{-4}$ |
| 5-(4-Methoxybenzyl)-2-mercaptoimidazole | 36% @ $10^{-4}$ |
| 5-(2-Phenylethyl)-2-mercaptoimidazole | $1.7 \times 10^{-5}$ |
| 5-(2-(4-Methoxyphenyl)ethyl)-2-mercaptoimidazole | 8.4% @ $10^{-4}$ |
| 5-(2-(4-Hydroxyphenyl)ethyl)-2-mercaptoimidazole | $4 \times 10^{-4}$ |
| 5-(3-(4-Methoxyphenyl)propyl)-2-mercaptoimidazole | 39% @ $10^{-4}$ |
| 5-(3-(4-Hydroxyphenyl)propyl)-2-mercaptoimidazole | 29% @ $10^{-4}$ |
| 5-(3-Phenylpropyl)-2-mercaptoimidazole | $1 \times 10^{-5}$ |
| 5-(4-(4-Methoxyphenyl)butyl)-2-mercaptoimidazole | $1 \times 10^{-4}$ |
| 5-(4-(4-Hydroxyphenyl)butyl)-2-mercaptoimidazole | 24% @ $10^{-4}$ |
| 5-(4-Phenylbutyl)-2-mercaptoimidazole | $1 \times 10^{-4}$ |

Further, spontaneously hypertensive rats were treated with 5-benzyl-2-mercaptoimidazole at a dose of 50 mg/kg intraperitoneally, and mean arterial blood pressure was monitored for 260 minutes using indwelling cannulae in the tail arteries. When compared to vehicle-treated controls, the animals treated with this compound exhibited significant blood pressure reductions within 30 minutes following treatment and exhibited their lowest blood pressures when monitoring was discontinued. The maximal blood pressure reduction was approximately 25 mmHg.

Formula II compounds are incorporated into convenient pharmaceutical dosage forms such as capsules, tablets, or injectable preparations. Solid or liquid pharmaceutical carriers can be employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid, or an aqueous or nonaqueous liquid suspension.

The pharmaceutical preparations are made following conventional techniques of a pharmaceutical chemist involving mixing, granulating and compressing, when necessary, for tablet forms, or mixing, filling, and dissolving the ingredients, as appropriate, to give the desired oral or parenteral products.

Doses of the present compounds of Formula II in a pharmaceutical dosage unit as described above will be an efficacious, nontoxic quantity selected from the range of 0.1–100 mg/kg of active compound, preferably 0.1–50 mg/kg. The selected dose is administered to a human patient in need of DBH inhibition from 1–6 times daily, orally, rectally, by injection, or continuously by infusion. Oral dosage units for human administration preferably contain from 1 to 500 mg of active compound. Parenteral administration, which uses lower dosages is preferred. Oral administration, at higher dosages, however, also can be used when safe and convenient for the patient.

The method of this invention of inhibiting DBH activity in mammals, including humans, comprises administering internally to a subject in need of such inhibition an effective DBH inhibiting amount of a Formula II compound.

The following examples are illustrative of preparation of Formula II compounds. The examples are not intended to limit the scope of the invention as defined hereinabove and as claimed below.

EXAMPLE 1

5-(4-Methoxybenzyl)-2-mercaptoimidazole

(i) 4-Methoxyphenylacetyl chloride

Thionyl chloride (200 ml) was added to 4-methoxyphenylacetic acid (78 g, 0.47 mole) followed by one drop of dimethylformamide. The reaction was heated at 65° C. for 4 hours and the solvent was removed under vacuum. The residue was distilled in vacuo (water aspirator) at 135° C. to give the product as a red oil (75.9 g, 88%).

(ii) 4-(4-Methoxyphenyl)-3-oxobutanoic acid, ethyl ester

4-Methoxyphenylacetyl chloride (76 g, 0.413 mole) was added to a stirred suspension of ethyl acetoacetate, sodium salt (62.8 g, 0.413 mole) in ether (250 ml) over a period of 1.5 hours and the reaction was allowed to sit for 3 days. The reaction mixture was treated with water (100 ml) and extracted with ether. The ether extract was cooled in an ice bath and ammonia gas was bubbled into the solution for 2.5 hours while the reactants were allowed to warm to room temperature. The reaction was washed with water, filtered and the ether fraction was stirred with 3N hydrochloric acid (100 ml) for 16 hours. The ether layer was washed with water, 5% sodium bicarbonate, brine and dried with sodium sulfate. The solvent was removed and the residue was distilled on a kugelrohr apparatus to give the product as a yellow oil (19.7 g, 20%).

(iii) 3-(4-Methoxyphenyl)-2-oxo-1-aminopropane, hydrochloride

Sodium nitrite (7.9 g, 100 mmole) in water (18 ml) was added to a solution of 4-(4-methoxyphenyl)-3-oxobutanoic acid, ethyl ester (19.7 g, 83.5 mmole) in acetic acid (15 ml) at such a rate to keep the temperature below 30° C. Ice (40 g) and acetic anhydride (21 ml) were added followed by the portionwise addition of zinc dust (13 g) while keeping the reaction temperature between 10°-20° C. The reaction was stirred for 2 hours while the mixture warmed to room temperature. The solids were removed by filtration and the filter cake was washed with water and methylene chloride. The combined filtrates were extracted with methylene chloride and the organic extracts were washed with water and 5% sodium carbonate. The emulsion was evaporated and the residue was heated under reflux with 3N hydrochloric acid (100 ml) for 16 hours. The reaction was cooled, extracted with methylene chloride and the organic extracts washed once with water. The combined aqueous fractions were evaporated and the residue was heated under reflux several times with ethyl alcohol to remove any residual water. The solvent was removed under vacuum and the residue was triturated with acetone and the mixture was filtered to give the product as a solid (3.12 g. 17%).

(iv) 5-(4-Methoxybenzyl)-2-mercaptoimidazole

A solution of 3-(4-methoxyphenyl)-2-oxo-1-aminopropane, hydrochloride (3.0 g, 14 mmole) and potassium thiocyanate (1.36 g, 14 mmole) in acetic acid (60 ml) was heated under reflux for 15 minutes. The reaction was cooled, diluted with water and the product was filtered and recrystallized from ethyl alcohol and dried to give the product was a solid (1.6 g, 52%).

EXAMPLE 2

5-(2-(4-Methoxyphenyl)ethyl)-2-mercaptoimidazole

(i) 3-(4-Methoxyphenyl)propionyl chloride

Thionyl chloride (200 ml) was added to -(4-methoxyphenyl)propionic acid (80 g, 0.44 mole) followed by one drop of dimethylformamide. The reaction was heated at 65° C. for 3 hours and the solvent was removed under vacuum. The residue was distilled in vacuo (water aspirator) at 143° C. to give the product as an oil (84.6 g, 97%).

(ii) 5-(4-Methoxyphenyl)-3-oxopentanoic acid, ethyl ester 3-(4-Methoxyphenyl)propionyl chloride (84.6 g, 0.426 mole) was added to a stirred suspension of ethyl acetoacetate, sodium salt (64.7 g, 0.426 mole) in ether (250 ml) over a period of 1.5 hours and the reaction was allowed to sit for 16 hours. The reaction mixture was treated with water (100 ml) and extracted with ether. The ether extract was cooled in an ice bath and ammonia gas was bubbled into the solution for 2.5 hours while the reactants were allowed to warm to room temperature. The reaction was washed with water, filtered and the ether fraction was stirred with 3N hydrochloric acid (100 ml) for 16 hours. The ether layer was washed with water, 5% sodium bicarbonate, brine and dried with sodium sulfate. The solvent was removed and the residue was distilled under high vacuum to give the product as an yellow oil (30.0 g, 28%).

(iii) 4-(4-Methoxyphenyl)-2-oxo-1-aminobutane, hydrochloride

Sodium nitrite (8.3 g, 120 mmole) in water (20 ml) was added to a solution of 5-(4-methoxyphenyl)-3-oxopentanoic acid, ethyl ester (30.0 g, 120 mmole) in acetic acid (20 ml) at such a rate to keep the temperature below 30° C. Ice (45 g) and acetic anhydride (21 ml) were added followed by the portionwise addition of zinc dust (13 g) while keeping the reaction temperature between 10°-20° C. The reaction was stirred for 2 hours while the mixture warmed to room temperature. The solids were removed by filtration and the filter cake was washed with water and methylene chloride. The combined filtrates were extracted with methylene chloride and the organic extracts were washed with water and 5% sodium carbonate. The organic portion was evaporated and the residue was heated under reflux with 3N hydrochloric acid (100 ml) for 16 hours. The reaction was cooled, extracted with methylene chloride and the organic extracts washed once with water. The combined aqueous fractions were evaporated and the residue was heated under reflux several times with ethyl alcohol to remove any residual water. The solvent was removed under vacuum and the residue was triturated with acetone and the mixture was filtered to give the product as a solid (3.1 g). An additional 6.3 g was recovered from the filtrate and combined with the first crop to give a total yield of 9.4 g, 45%.

(iv) 5-(4-Methoxyphenethyl)-2-mercaptoimidazole

A solution of 4-(4-methoxyphenyl)-2-oxo-1-aminobutane, hydrochloride (8.6 g, 37.7 mmole) and potassium thiocyanate (3.6 g, 37.7 mmole) in acetic acid (100 ml) was heated under reflux for 20 minutes. The reaction was cooled, diluted with water and the product was filtered and recrystallized from ethyl alcohol and dried to give the product as a solid (1.7 g, 19%).

EXAMPLE 3

5-(4-Chlorophenyl)-2-mercaptoimidazole

The procedure of Example 1 wherein 4-methoxyphenylacetic acid is replaced by 4-chlorobenzoic acid yields 5-(4-chlorophenyl)-2-mercaptoimidazole, m.p. 308° C.

EXAMPLE 4

5-(4-Hydroxyphenyl)-2-mercaptoimidazole

The Example 1 process wherein 4-methoxyphenyl acetic acid is replaced by 4-methoxybenzoic acid yields (4-methoxyphenyl)-2-mercaptoimidazole, m.p. 204° C. Treatment of this compound in methylene chloride with boron tribromide yields 5-(4-hydroxyphenyl)-2-mercaptoimidazole, m.p. 307° C. (dec).

EXAMPLE 5

5-(4-Phenylethyl)-2-mercaptoimidazole

The Example 1 process wherein 4-methoxyphenylacetic acid is replaced by 3-phenylpropionic acid yields (4-phenylethyl)-2-mercaptoimidazole, m.p. 185°–186° C.

EXAMPLE 6

5-(4-Hydroxybenzyl)-2-mercaptoimidazole with boron tribromide yields 5-(4-hydroxybenzyl)mercaptoimidazole, m.p. 246°–248° C.

EXAMPLE 7

5-(2-(4-Hydroxyphenyl)ethyl)-2-mercaptoimidazole

Treatment of 5-(2-(4-methoxyphenyl)ethyl)-2-mercaptoimidazole, prepared as in Example 2, in methylene chloride with boron tribromide yields 5-(2-(4-hydroxyphenyl)ethyl)-2-mercaptoimidazole, m.p. 210°–212° C.

EXAMPLE 8

5-(3-(4-Methoxyphenyl)propyl)-2-mercaptoimidazole

The Example 1 procedure wherein 4-methoxyphenylacetic acid is replaced by 3-(4-methoxyphenyl)-butyric acid yields 5-(3-(4-methoxyphenyl)propyl)-2-mercaptoimidazole, m.p. 165°–167° C.

EXAMPLE 9

5-(3-(4-Hydroxyphenyl)propyl)-2-mercaptoimidazole

Treatment of 5-(3-(4-methoxyphenyl)propyl)-2-mercaptoimidazole, prepared as in Example 8, in methylene chloride with boron tribromide yields 5-(3-(4-hydroxyphenyl)propyl)-2-mercaptoimidazole, m.p. 189°–190° C.

EXAMPLE 10

5-(3-Phenylpropyl)-2-mercaptoimidazole

The Example 1 process wherein 4-methoxyphenylacetic acid is replaced by 3-phenylbutyric acid yields (3-phenylpropyl)-2-mercaptoimdazole, m.p. 143° C.

EXAMPLE 11

5-(4-(4-Methoxyphenyl)butyl)-2-mercaptoimidazole

The Example 1 procedure wherein 4-methoxyphenylacetic acid is replaced by 5-(4-methoxyphenyl)-pentanoic acid yields 5-(4-(4-methoxyphenyl)butyl)-2-mercaptoimidazole, m.p. 170°–171° C.

EXAMPLE 12

5-(4-(4-Hydroxyphenyl)butyl)-2-mercaptoimidazole

Treatment of 5-(4-(4-methoxyphenyl)butyl)-2-mercaptoimidazole, prepared as in Example 11, in methylene chloride with boron tribromide yields 5-(4-(4-hydroxyphenyl)butyl)-2-mercaptoimidazole, m.p. 179°–180° C.

EXAMPLE 13

5-(4-Phenylbutyl)-2-mercaptoimidazole

The process of Example 1 wherein 4-methoxyphenylacetic acid is replaced by 5-phenylpentanoic acid yields 5-(4-phenylbutyl)-2-mercaptoimidazole, m.p. 168°–169° C.

EXAMPLE 14

5-(3,5-Difluoro-4-methoxybenzyl)-2-mercaptoimidazole

The Example 1 process wherein 4-methoxyphenylacetic acid is replaced by 3,5-difluoro-4-methoxyphenylacetic acid yields 5-(3,5-difluoro-4-methoxybenzyl)-2-mercaptoimidazole.

EXAMPLE 15

5-(2,4,6-Trichloro-3-methoxy-5-trifluoromethylbenzyl)-2-mercaptoimidazole

The Example 1 procedure wherein 4-methoxyphenylacetic acid is replaced by 2,4,6-trichloro-3-methoxy-5-trifluoromethylphenylacetic acid yields 5-(2,4,6-trichloro-3-methoxy -5-trifluoromethylbenzyl)-2-mercaptoimidazole.

EXAMPLE 16

5-(4-Cyanobenzyl)-2-mercaptoimidazole

The Example 1 process wherein 4-methoxyphenylacetic acid is replaced by 4-cyanophenylacetic acid yields 5-(4-cyanobenzyl)-2-mercaptoimidazole.

EXAMPLE 17

5-(4-Nitrobenzyl)-2-mercaptoimidazole

The Example 1 process wherein 4-methoxyphenylacetic acid is replaced by 4-nitrophenylacetic acid yields 5-(4-nitrobenzyl)-2-mercaptoimidazole.

EXAMPLE 18

5-(4-Hydroxymethylbenzyl)-2-mercaptoimidazole

The Example 1 procedure wherein 4-methoxyphenylacetic acid is replaced by 4-hydroxymethylphenylacetic acid yields 5-(4-hydroxymethylbenzyl)-2-mercaptoimidazole.

EXAMPLE 19

5-(4-Methoxybenzyl)-2-methylmercaptoimidazole

Treatment of 5-(4-methoxybenzyl)-2-mercaptoimidazole prepared as in Example 1 with methyl iodide in methanol by known techniques yields 5-(4-methoxybenzyl)-2-methylmercaptoimidazole.

EXAMPLE 20

An oral dosage form for administering the presently invented compounds is produced by screening, and filling into hard gelatin capsules the redients in the proportions shown in Table II, below.

TABLE II

| Ingredients | Amounts |
| --- | --- |
| 5-(3,5-Difluorobenzyl)-2-mercaptoimidazole | 50 mg |
| magnesium stearate | 5 mg |
| lactose | 75 mg |

EXAMPLE 21

The sucrose, calcium sulfate dihydrate, and Formula II compound shown in Table III below, are mixed ranulated in the proportions shown with a 10% gelatin solution. The wet granules are screened, dried, mixed with the starch, talc and stearic acid, screened and compressed into a tablet.

TABLE III

| Ingredients | Amounts |
| --- | --- |
| 5-(3,5-Dichlorobenzyl)-2-mercaptoimidazole | 100 mg |
| calcium sulfate dihydrate | 150 mg |
| sucrose | 20 mg |
| starch | 10 mg |
| talc | 5 mg |
| stearic acid | 3 mg |

EXAMPLE 22

5-(3,5-Dichlorobenzyl)-2-mercaptoimidazole hydrochloride, 75 mg, is dispursed in 25 ml of normal saline to prepare an injectable preparation.

Contemplated equivalents of Formula II compounds are compounds that upon administration to mammals, including humans, are metabolized to Formula II compounds or metabolized to any Formula II compound active metabolites at a sufficient rate and in sufficient amounts to produce physiologic activity of Formula II compounds. Such compounds also would be included in the invented pharmaceutical compositions and used in the invented methods.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound of the formula:

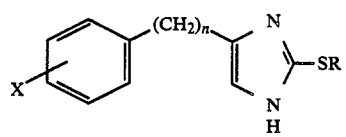

in which:
X is H, F, Cl, Br, I, $C_{1-4}$ alkyl, CN, $NO_2$, $SO_2NH_2$, COOH, OH, CHO, $C_{1-4}$ alkoxy, $CH_2OH$, $CH_2OC_{1-4}$ alkyl, $CF_3$, $C_2F_5$, $C_3F_7$, $SO_2CH_3$, $SO_2CF_3$, or $CO_2C_aH_{2a+1}$ wherein a is 1–5, or any accessible combination thereof of up to 5 substituents;

R is H or $C_{1-4}$ alkyl; and n is 1–5; or any pharmaceutically acceptable salt or hydrate thereof, with the proviso that when X is H, n is not 1–3 and when X is one F, Cl, Br or I, n is not 1 or 2.

2. A compound of claim 1 wherein R is H.

3. A compound of claim 2 wherein n is 1.

4. The compound of claim 3 that is 5-(3,5-difluorobenzyl)-2-mercaptoimidazole.

5. A compound of claim 3 that is 5-(4-methyoxybenzyl)-2-mercaptoimidazole or 5-(4-hydroxybenzyl)-2-mercaptoimidazole.

6. A compound of claim 2 wherein n is 2.

7. A compound of claim 6 that is 5-(2-(4-methoxyphenyl)ethyl)-2-mercaptoimidazole or 5-(2-(4-hydroxyphenyl)ethyl)-2-mercaptoimidazole.

8. A compound of claim 2 wherein n is 3.

9. A compound of claim 8 that is 5-(3-(4-methoxyphenyl)propyl)-2-mercaptoimidazole or 5-(3-(4-hydroxyphenyl)propyl)-2-mercaptoimidazole.

10. A compound of claim 2 wherein n is 4.

11. A compound of claim 10 that is 5-(4-phenylbutyl)-2-mercaptoimidazole, 5-(4-(4-methoxyphenyl)butyl)-2-mercaptoimidazole, or 5-(4-(4-hydroxyphenyl)butyl)-2-mercaptoimidazole.

12. A pharmaceutical composition having dopamine-β-hydroxylase inhibiting activity comprising a pharmaceutical carrier and a compound of the formula:

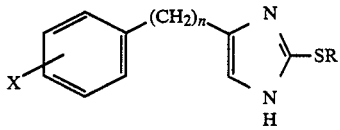

in which
X is H, F, Cl, Br, I, $C_{1-4}$ alkyl, CN, $NO_2$, $SO_2NH_2$, COOH, OH, CHO, $C_{1-4}$ alkoxy, $CH_2OH$, $CH_2OC_{1-4}$ alkyl, $CF_3$, $C_2F_5$, $C_3F_7$, $SO_2CH_3$, $SO_2CF_3$, or $CO_2C_aH_{2a+1}$ wherein a is 1–5, or any accessible combination thereof of up to 5 substituents;

R is H or $C_{1-4}$ alkyl; and n is 1–5; or any pharmaceutically acceptable salt or hydrate thereof, with the proviso that when X is H, n is not 1–3 and when X is one F, Cl, Br or I, n is not 1 or 2.

13. A composition of claim 12 in which the compound is 5-(3,5-difluorobenzyl)-2-mercaptoimidazole.

14. A pharmaceutical composition of claim 12 wherein the compound is 5-(4-methoxybenzyl)-2-mercaptimdazole, 5-(4-hydroxybenzyl)2-mercaptoimidazole, 5-(2-(4-methoxyphenyl)ethyl)-2-mercaptoimidazole, 5-(2-(4-hydroxyphenyl)ethyl)-2-mercaptoimidazole, 5-(3-(4-methoxyphenyl)propyl)-2-mercaptoimidazole, 5-(3-(4-hydroxyphenyl)propyl)-2-mercaptoimidazole, 5-(4-phenylbutyl)2-mercaptoimidazole, 5-(4-(4-methoxyphenyl)butyl)2-mercaptoimidazole, or 5-(4-(4-hydroxyphenyl)butyl)-2-mercaptoimidazole.

15. A method of inhibiting dopamine-β-hydroxylase activity in mammals that comprises administering an effective amount of a compound of the formula:

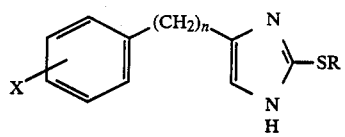

in which:
X is H, F, Cl, Br, I, $C_{1-4}$ alkyl, CN, $NO_2$, $SO_2NH_2$, COOH, OH, CHO, $C_{1-4}$ alkoxy, $CH_2OH$, $CH_2OC_{1-4}$ alkyl, $CF_3$, $C_2F_5$, $C_3F_7$, $SO_2CH_3$, $SO_2CF_3$, or $CO_2C_aH_{2a+1}$ wherein a is 1-5, or any accessible combination thereof of up to 5 substituents;
R is H or $C_{1-4}$ alkyl; and
n is 0-5; or
any pharmaceutically acceptable salt or hydrate thereof.

16. The method of claim 15 in which the compound is 5-(3,5-difluyorobenzyl)-2-mercaptoimidazole.

17. A method of claim 15 wherein the compound is 5-(4-methoxybenzyl)2-mercaptoimidazole, 5-(4-hydroxybenzyl)-2-mercaptoimidazole, 5-(2-phenylethyl)-2-mercaptoimidazole, 5-(2-(4-methoxyphenyl)ethyl)-2-mercaptoimiazole, 5-(2-(4-hydroxyphenyl)ethyl)-2-mercaptoimidazole, 5-(3-phenylpropyl)-2-mercaptoimidazole, 5-(3-(4-methoxyphenyl)propyl)-2-mercaptoimidazole, 5-(3-(4-hydroxyphenyl)propyl)-2-mercaptoimidazole, 5-(4-phenylbutyl)-2-mercaptoimidazole, 5-(4(4-methyoxyphenyl)butyl)-2-mercaptoimidazole, 5-(4-(4-hydroxyphenyl)butyl)-2-mercaptoimidazole, 5-(4-chlorophenyl)-2-mercaptoimidazole, 5-(4-methoxyphenyl)-2-mercaptoimidazole, or 5-(4-hydroxyphenyl)-2-mercaptoimidazole.

18. A method of reducing blood pressure in mammals that comprises adminstering an effective amount of a compound of the formula:

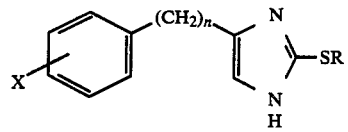

in which:
X is X, F, Cl, Br, I, $C_{1-4}$ alkyl, CN, $NO_2$, $SO_2NH_2$, COOH, OH, CHO, $C_{1-4}$ alkoxy, $CH_2OH$, $CH_2OC_{1-4}$ alkyl, $CF_3$, $C_2F_5$, $C_3F_7$, $SO_2CH_3$, $SO_2CF_3$, or $CO_2C_aH_{2a+1}$ wherein a is 1-5, or any accessible combination thereof of up to 5 substituents;
R is H or $C_{1-4}$ alkyl; and
n is 0-5; or
any pharmaceutically acceptable salt or hydrate thereof.

* * * * *

UNITED STATES PATENT AND TRADEMARK OFFICE
CERTIFICATE OF CORRECTION

PATENT NO. : 4,798,843
DATED : January 17, 1989
INVENTOR(S) : Lawrence Ivan Kruse It is certified that error appears in the above-identified patent and that said Letters Patent is hereby corrected as shown below:

In the Title, on the cover page, and at column 1, line 2, replace "2-MERCAPROIMIDAZOLE" with --2-MERCAPTOIMIDAZOLE--.

In Claim 16, at column 13, line 23, replace "5-(3,5-difluyoro-benzyl)" with --5-(3,5-difluorobenzyl)--.

In Claim 18, at column 14, line 20, replace "X is X," with --X is H,--.

Signed and Sealed this

First Day of August, 1989

*Attest:*

DONALD J. QUIGG

*Attesting Officer*   *Commissioner of Patents and Trademarks*